United States Patent [19]

Okada et al.

[11] 4,424,214
[45] Jan. 3, 1984

[54] INSECTICIDAL PYRAZOLYL PHOSPHATES

[75] Inventors: Yoshiyuki Okada, Osaka; Yasuo Sato, Kyoto, Japan

[73] Assignee: Takeda Chemical Industries, Inc., Osaka, Japan

[21] Appl. No.: 367,608

[22] Filed: Apr. 12, 1982

Related U.S. Application Data

[63] Continuation of Ser. No. 75,842, Sep. 14, 1979, abandoned.

[30] Foreign Application Priority Data

Sep. 19, 1978 [JP] Japan .................. 53-115536

[51] Int. Cl.³ .................. A01N 57/16; C07F 9/65
[52] U.S. Cl. .................. 424/200; 548/116; 548/363; 548/365
[58] Field of Search .................. 548/116; 424/200

[56] References Cited

U.S. PATENT DOCUMENTS 4,163,052 7/1979 Hofer et al. .................. 548/377

FOREIGN PATENT DOCUMENTS 184580 2/1956 Austria.

Primary Examiner—Richard A. Schwartz
Attorney, Agent, or Firm—Wenderoth, Lind & Ponack

[57] ABSTRACT

Pyrazolyl phosphates of the formula

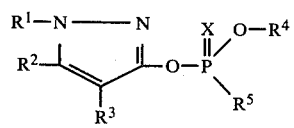

wherein $R^1$ is alkyl, aralkyl, or phenyl which may optionally be substituted by halogen or lower alkyl; $R^2$ is hydrogen or lower alkyl; $R^3$ is hydrogen, halogen, nitro, lower alkyl or $-COOR^6$ wherein $R^6$ is lower alkyl; $R^4$ is lower alkyl; $R^5$ is lower alkylthio; and X is oxygen or sulfur, have marked insecticidal-acaricidal activity against household pests, plant pests and mites, without substantial toxicity to warm-blooded animals and fish.

14 Claims, No Drawings

INSECTICIDAL PYRAZOLYL PHOSPHATES

This application is a continuation of application Ser. No. 075,842, filed Sept. 14, 1979 (now abandoned).

This invention relates to novel pyrazolyl phosphates, a method for producing the same and insecticidal-acaricidal compositions containing the same.

More particularly, the invention relates to pyrazolyl phosphates, a method for producing the same and insectididal-acaricidal compositions containing the same, said pyrazolyl phosphates having the general formula (I):

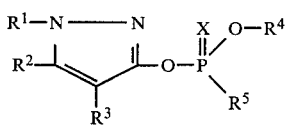

wherein $R^1$ is alkyl, aralkyl, or phenyl which may optionally be substituted by lower alkyl or halogen; $R^2$ is hydrogen or lower alkyl; $R^3$ is hydrogen, halogen, nitro, lower alkyl or $-COOR^6$ wherein $R^6$ is lower alkyl; $R^4$ is lower alkyl; $R^5$ is lower alkylthio; and X is oxygen or sulfur.

For the purpose of developing an insecticide or acaricide which could be produced profitably on a commercial scale and could be safely applied without substantial toxicity to warm-blooded animals and fish, without presenting any substantial drug damage to plants, the present inventors synthesized many organic compounds and examined them by performing biological and other tests. As a result they found that compounds of the general formula (I) presented hereinbefore have marked insecticidal-acaricidal activity against household pests, plant pests and mites and can be produced profitably on a commercial scale.

Referring, now, to general formula (I), the alkyl group $R^1$ is a straight-chain, branched or cyclic alkyl group of 1 to 10 carbon atoms, such as methyl, ethyl, n-propyl, isopropyl, n-butyl, isobutyl, sec.-butyl, n-pentyl, isopentyl, cyclopentyl, n-hexyl, cyclohexyl, n-heptyl, n-octyl, n-nonyl, n-decyl, etc. The aralkyl $R^1$ may for example be benzyl or phenethyl. $R^1$ may alternatively be a phenyl group substituted by lower alkyl or halogen. The lower alkyl mentioned just above and the lower alkyl groups $R^2$, $R^3$, $R^4$ and $R^6$ each is a straight-chain or branched alkyl of 1 to 4 carbon atoms, such as methyl, ethyl, n-propyl, isopropyl, n-butyl, isobutyl or sec.-butyl. The lower alkylthio $R^5$ may for example be methylthio, ethylthio, n-propylthio, isopropylthio, n-butylthio, isobutylthio or sec.-butylthio, although n-propylthio is especially desirable. The halogen on substituted phenyl $R^1$ and the halogen $R^3$ may each be fluorine, chlorine, bromine or iodine, although fluorine, chlorine or bromine is desirable.

Where the substituted phenyl $R^1$ has a plurality of substituents, such substituents may be the same or different. As examples of such substituted phenyl may be mentioned 2,4-dichlorophenyl, 2,6-dichlorophenyl, 3,4-dichlorophenyl, 3,5-dichlorophenyl, 2,4,5-trichlorophenyl, 2,4,6-trichlorophenyl, 2,4-dibromophenyl, 4-bromo-2-chlorophenyl, 4-chloro-2-fluorophenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 3-chloro-4-methylphenyl, 3-chloro-2-methylphenyl, 4-chloro-2-methylphenyl, 5-chloro-2-methylphenyl, 2-bromo-4-methylphenyl, 4-bromo-2-methylphenyl, 4-bromo-2,6-dimethylphenyl, etc.

Especially important among the compounds (I) of this invention are the compounds wherein $R^4$ is ethyl, $R^5$ is n-propylthio, and $R^1$, $R^2$, $R^3$ and X are as defined hereinbefore.

Particularly interesting among the compounds (I) of this invention are the compounds wherein $R^4$ is ethyl, $R^5$ is n-propylthio, X is oxygen and $R^1$, $R^2$ and $R^3$ are as defined hereinbefore.

A still desirable class of compounds (I) comprises compounds wherein $R^4$ is ethyl, $R^5$ is n-propylthio, X is oxygen, $R^1$ is methyl, ethyl, n-propyl, isopropyl, n-butyl, sec-butyl, isobutyl, cyclohexyl, benzyl, phenyl, 4-chlorophenyl or 4-methylphenyl; $R^2$ is hydrogen and $R^3$ is hydrogen, methyl, chlorine or bromine.

Of compounds according to this invention, the most important are the compounds in which $R^4$ is ethyl and $R^5$ is n-propylthio. This class of compounds is characterized in that they have marked insecticidal-acaricidal activity and relatively low oral acute toxicity to warm-blooded animals. This tendency toward low toxicity is marked where $R^1$ is phenyl or substituted phenyl.

Moreover, this class of compounds not only have a broad insecticidal spectrum covering a variety of insects but display especially marked controlling activity against insects of the order Lepidoptera and mites. This activity manifests not only when the compound of this invention is directly applied to pests, for example by spraying it on host plants, but also when the compound (I) absorbed by plants from the roots, leaves, stems or the like comes into contact with pests as, for example, the latter suck or gnaw the plant. This penetrative insecticidal effect is particularly marked when $R^1$ is alkyl.

The compound (I) according to this invention may be produced by procedures known per se. For example, it can be produced by esterifying a compound of general formula (II) or a salt thereof with a compound of general formula (III).

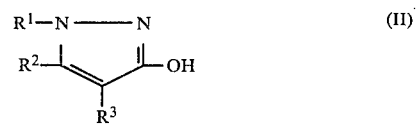

(wherein $R^1$, $R^2$ and $R^3$ are as defined hereinbefore)

(wherein W is $OR^4$ or Y; Y is halogen; $R^4$ and $R^5$ are as defined hereinbefore) This esterification reaction is preferably conducted in the presence of an acid acceptor.

As said acid acceptor, there may be mentioned tertiary amines (e.g. trialkylamine, pyridine, γ-collidine, etc.); the hydroxides, oxides, carbonates and bicarbonates of alkali metals or alkaline earth metals and the alkoxides of alkali metals (e.g. sodium carbonate, potassium carbonate, sodium hydrogen carbonate, sodium hydroxide, potassium hydroxide, sodium methoxide sodium ethoxide, etc.)

The salt of 3-hydroxypyrazole compound (II) is desirably an alkali metal salt such as the sodium salt or potassium salt, for instance. Generally the reaction is preferably carried out in an inert solvent, suitable inert solvents including aromatic hydrocarbons (benzene, toluene, xylene, etc.), halogenated hydrocarbons (e.g. methylene chloride, chloroform, carbon tetrachloride, etc.), ethers (e.g. ethyl ether, dioxane, tetrahydrofuran, etc.), ketones (e.g. acetone methyl ethyl ketone, etc.), nitriles (e.g. acetonitrile, etc.), acid amides (e.g. dimethylformamide, etc.), esters (e.g. ethyl acetate, etc.) and sulfoxides (e.g. dimethylsulfoxide, etc.)

The reaction is conducted at a suitable temperature from $-20°$ to $+150°$ C. Normally, such suitable temperature lies somewhere between $0°$ and $100°$ C.

The reaction goes to completion in 30 minutes to 6 hours. The end-point of reaction can be ascertained by a known technique such as thin layer chromatography.

On completion of the reaction, the desired compound can be isolated by procedures known per se.

For example, the reaction mixture as such is washed with water or, after the solvent has been removed, the residue is extracted with an organic solvent and washed with water. It is then dried, e.g. over anhydrous sodium sulfate, and the solvent is distilled off. The desired compound may then be further purified by distillation, recrystallization, column chromatography, etc.

In the foregoing reaction, when a compound (III) wherein the symbol W represents Y is employed, a compound of the formula

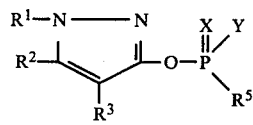

wherein $R^1$, $R^2$, $R^3$, $R^5$, X and Y are as defined hereinbefore is obtained, which is further reacted with a compound of formula $R^4OH$ ($R^4$ is as defined hereinbefore) to obtain the compound (I).

The material compounds used in these reactions can be easily produced by known reaction procedures or by procedures analogous thereto.

The compound (I) according to this invention is effective in the control of household pests, plant parasitic insects and mites.

More particularly, the compound (I) as well as any suitable composition containing compound (I) is particularly effective in the control of pests including, but not limited thereto, insects of the order Hemiptera such as *Eurydema rugosa, Scotinophara lurida, Riptortus clavatus, Stephanitis nashi, Laodelphax striatellus, Nephotettix cincticeps, Unaspis yanonensis, Aphis glycines, Lipaphis pseudobrassicae, Brevicoryne brassicae* and *Aphis gossypii;* insects of the order Lepidoptera such as *Spodoptera litura, Plutella maculipennis, Pieris rape crucivora, Chilo suppressalis, Plusia nigrisigna, Helicoverpa assulta Guenee, Leucania separata, Mamestra brassicae, Adoxophyes orana, Syllepte derogata, Cnaphalocrocis medinalis* and *Phthorimaea operculella;* insects of the order Coleptera such as *Epilachna vigintioctopunctata, Aulacophora femoralis, Phyllotreta striolata, Oulema orgzae* and *Echinocnemus squameus;* insects of the order Diptera such as *Masca domestica vicina, Culex pipiens pallens, Tabanus trigonus, Hylemya antiqua,* and *Hylemya platura;* insects of the order Orthoptera such as *Locusta migratoria, Gryllotalpa africana;* insects of the order Blattariae such as *Blattella germanica* and *Periplaneta fuliginosa;* mites such as *Tetranychus urticae, Panonychus citri, Tetranychus kanzawai, Tetranychus cinnabarinus, Panonychus ulmi* and *Aculops pelekassi;* and nematodes such as *Aphelenchoides besseyi,* etc.

For use as an insecticidal-acaricidal agent, the compound (I) according to this invention may take any of the known application formulations of agricultural chemicals. Thus, for example, one or more species of compound (I) are dissolved or dispersed in a suitable liquid carrier or admixed with, or adsorbed on, a suitable solid carrier to prepare an emulsifiable concentrate, oil solution, wettable powder, dust, granule, tablet, spray or the like. If necessary, emulsifiers, suspension aids, spreading agents, penetrating agents, wetting agents, thickeners, stabilizers, etc. may also be incorporated in such compositions. These preparations can be produced by known manufacturing methods.

The concentration of active compound (I) in such an insecticidal-acaricidal composition may vary with intended uses. Thus, while the concentration may desirably be in the range of about 10 to 90 weight % in the case of emulsifiable concentrates, wettable powders, etc., about 0.1 to 10 weight % in the case of oil solutions, dusts, etc. and about 1 to 20 weight % in the case of granules, these concentrations may be modified according to the intended application. As for emulsifiable concentrates, wettable powders, etc., they are applied after diluting (e.g. 100 to 100000-fold) at site using a diluent such as water.

As examples of said liquid carrier, there may be mentioned water, alcohols (e.g. methyl alcohol, ethyl alcohol, ethylene glycol, etc.), ketones (e.g. acetone, methyl ethyl ketone, etc.), ethers (e.g. dioxan, tetrahydrofuran, cellosolve, etc.), aliphatic hydrocarbons (e.g. gasoline, kerosin, kerosene, fuel oil, machine oil, etc.), aromatic hydrocarbons (e.g. benzene, toluene, xylene, solvent naphtha, methylnaphthalene, etc.), halogenated hydrocarbons (e.g. chloroform, carbon tetrachloride, etc.), acid amides (e.g. dimethylformamide, etc.), esters (e.g. ethyl acetate, butyl acetate, fatty acid glycerides, etc.), nitriles (e.g. acetonitrile, etc.) and so on. These solvents may be used alone or as a mixture of two or more species.

As examples of said solid carrier, there may be mentioned vegetable powders (e.g. soybean powder, tobacco powder, wheat flour, sawdust, etc.), mineral powders (e.g. clays such as kaolin, bentonite, acid clay, etc.; talcs such as talcum powder, agalmatolite, etc.; diatomaceous earth, mica powder and other siliceous materials), alumina, sulfur powder, activated carbon, etc. These solid carriers are used alone or as a mixture of two or more species.

There may also be employed ointment bases such as polyethylene glycol, pectin, polyhydric alcohol esters of higher fatty acids (e.g. glycerol monostearate), cellulose derivatives (e.g. methylcellulose), sodium alginate, bentonite, higher alcohols, polyhydric alcohols (e.g. glycerin), vaseline, white petrolatum, liquid paraffin, lard, vegetable oils, lanolin, anhydrous lanolin, hydrogenated oils, resins, etc. These bases may contain various surfactants and other additives.

The surfactants which may be used as said emulsifiers, extenders, penetrating agents, dispersing agents, etc. include soaps, polyoxyalkylene-aryl esters (e.g. Nornal ®, Takemoto Yushi K.K., Japan), alkylsulfates (e.g. Emal 10 ® & Emal 40 ®, Kao-Atlas K.K., Japan), alkylsulfonates (e.g. Neogen ® & Neogen T ®, Diichi Kogyo Seiyaku K.K., Japan; Neoperex ®, Kao-Atlas K.K., Japan), polyethylene glycol ethers (e.g. Nonipol 85 ®, Nonipol 100 ® & Nonipol 160 ®, Sanyo Chemical Industries, Ltd., Japan); polyhydric alcohol esters (e.g. Tween 20 ® & Tween 80 ®, Kao-Atlas K.K., Japan), etc. The compound (I) of this invention may also be used in admixture with other insectides (pyrethroid, organophosphorus, carbamate, natural and other insectides), miticides, nematocides, herbicides, plant hormones, plant growth regulators, fungicides (e.g. copper, organochlorine, organosulfur, phenolic and other fungicides), synergists, attractants, repellents, colorants, fertilizers, etc.

The composition containing the compound (I) can be employed to control the above-mentioned insects or mites attacking for example, dry field harvest, such as cabbages, soy beans, maize, cotton, and tobacco; fruit trees of apples, oranges, etc. The composition can also be applied to the inside and outside of cattle barns or poultry houses. The amount of the effective component to be used is usually within the range of from ca. 100 g to ca. 10 Kg per ha., preferably from ca. 300 g to ca. 3 Kg per ha.

The following examples are intended to illustrate this invention is further detail and should by no means be construed to delimit the scope of the invention.

EXAMPLE 1

O-ethyl-S-n-propyl-O-(1-isopropyl-4-methylpyrazol-3-yl)phosphorothiolate (Compound No. 13)

In 60 ml of methyl ethyl ketone is suspended 3.2 g (0.02 mol) of 1-isopropyl-3-hydroxy-4-methylpyrazole sodium salt, followed by addition of 4.0 g (0.02 mol) of O-ethyl S-n-propyl phosphorochloridothiolate. The mixture is stirred at room temperature for 3 hours. On completion of the reaction, the methyl ethyl ketone is distilled off, toluene is added to the residue and the toluene layer is washed with water and dried over anhydrous sodium sulfate. The toluene is distilled off and the residue is purified by silica gel chromatography (eluent: chloroform). By the above procedure is obtained 4.3 g of colorless, clear oil.

$n_D^{25}$ 1.4860

EXAMPLE 2

O-ethyl-S-n-propyl-O-(1-phenyl-4-chloropyrazol-3-yl) phosphorothiolate (Compound No. 30)

In 100 ml of acetone is suspended 4.3 g (0.02 mol) of 1-phenyl-3-hydroxy-4-chloropyrazole sodium salt, followed by addition of 4.0 g (0.02 mol) of O-ethyl-S-n-propyl phosphorochloridothiolate. The mixture is stirred at room temperature for 3 hours. On completion of the reaction the acetone is distilled off. Thereafter the residue is treated as in Example 1. By the above procedure is obtained 5.4 g of colorless clear oil.

$n_D^{20}$ 1.5616

Table 1, below, lists the compounds synthesized in generally the same manner as Example 1 or 2, inclusive of the compounds produced in Examples 1 and 2.

TABLE 1

$$R^1-N-N \quad \begin{matrix} X & O-R^4 \\ \| & / \\ R^2-\underset{R^3}{\overset{\|}{\diagdown}}-O-P \\ & \diagdown R^5 \end{matrix}$$

| No. | $R^1$ | $R^2$ | $R^3$ | $R^4$ | $R^5$ | X | Physical Constant |
|---|---|---|---|---|---|---|---|
| 1 | $CH_3$ | H | H | $C_2H_5$ | $SC_3H_7(n)$ | O | $n_D^{20}$ 1.4966 |
| 2 | $CH_3$ | H | $CH_3$ | $C_2H_5$ | $SC_3H_7(n)$ | O | $n_D^{22}$ 1.4960 |
| 3 | $CH_3$ | H | $CH_3$ | $C_2H_5$ | $SC_3H_7(n)$ | S | $n_D^{24}$ 1.5325 |
| 4 | $C_2H_5$ | H | H | $C_2H_5$ | $SC_3H_7(n)$ | O | $n_D^{20}$ 1.4952 |
| 5 | $C_2H_5$ | H | Br | $C_2H_5$ | $SC_3H_7(n)$ | O | $n_D^{24}$ 1.5143 |
| 6 | $C_2H_5$ | H | Cl | $C_2H_5$ | $SC_3H_7(n)$ | O | $n_D^{21}$ 1.5005 |
| 7 | $C_2H_5$ | H | $CH_3$ | $C_2H_5$ | $SC_3H_7(n)$ | O | $n_D^{21}$ 1.4919 |
| 8 | $C_3H_7(n)$ | H | $CH_3$ | $C_2H_5$ | $SC_3H_7(n)$ | O | $n_D^{24}$ 1.4880 |
| 9 | $C_3H_7(i)$ | H | $CH_3$ | $C_2H_5$ | $SC_2H_5$ | O | $n_D^{20}$ 1.4896 |
| 10 | $C_3H_7(i)$ | H | H | $C_2H_5$ | $SC_3H_7(n)$ | O | $n_D^{20}$ 1.4870 |
| 11 | $C_3H_7(i)$ | H | Br | $C_2H_5$ | $SC_3H_7(n)$ | O | $n_D^{27}$ 1.5042 |
| 12 | $C_3H_7(i)$ | H | Cl | $C_2H_5$ | $SC_3H_7(n)$ | O | $n_D^{27}$ 1.4952 |
| 13 | $C_3H_7(i)$ | H | $CH_3$ | $C_2H_5$ | $SC_3H_7(n)$ | O | $n_D^{25}$ 1.4860 |
| 14 | $C_3H_7(i)$ | H | $CH_3$ | $C_2H_5$ | $SC_3H_7(n)$ | S | $n_D^{20}$ 1.5195 |
| 15 | $C_3H_7(i)$ | H | $-COOC_2H_5$ | $C_2H_5$ | $SC_3H_7(n)$ | O | $n_D^{20}$ 1.4919 |
| 16 | $C_4H_9(s)$ | H | H | $C_2H_5$ | $SC_3H_7(n)$ | O | $n_D^{24}$ 1.4846 |
| 17 | $C_4H_9(s)$ | H | Br | $C_2H_5$ | $SC_3H_7(n)$ | O | $n_D^{21}$ 1.5052 |
| 18 | $C_4H_9(s)$ | H | $CH_3$ | $C_2H_5$ | $SC_3H_7(n)$ | O | $n_D^{24}$ 1.4865 |
| 19 | $C_4H_9(i)$ | H | H | $C_2H_5$ | $SC_3H_7(n)$ | S | $n_D^{24}$ 1.5195 |
| 20 | $C_4H_9(i)$ | H | Br | $C_2H_5$ | $SC_3H_7(n)$ | O | $n_D^{25}$ 1.5033 |
| 21 | $C_4H_9(i)$ | H | $CH_3$ | $C_2H_5$ | $SC_3H_7(n)$ | O | $n_D^{24}$ 1.4837 |
| 22 | ⟨H⟩ | H | H | $C_2H_5$ | $SC_3H_7(n)$ | O | $n_D^{23}$ 1.4986 |
| 23 | ⟨H⟩ | H | Br | $C_2H_5$ | $SC_3H_7(n)$ | O | $n_D^{23}$ 1.5269 |
| 24 | ⟨H⟩ | H | $CH_3$ | $C_2H_5$ | $SC_3H_7(n)$ | O | $n_D^{24}$ 1.5014 |

TABLE 1-continued $$\begin{array}{c} R^1-N-N \\ R^2 \diagdown \phantom{xxx} \diagup O-P \diagup\!\!\!\diagdown O-R^4 \\ \phantom{xx} R^3 \phantom{xxxxx} R^5 \end{array}$$

| No. | R¹ | R² | R³ | R⁴ | R⁵ | X | Physical Constant |
|---|---|---|---|---|---|---|---|
| 25 | C₆H₅—CH₂— | H | H | C₂H₅ | SC₃H₇(n) | O | $n_D^{27}$ 1.5308 |
| 26 | C₆H₅— | H | Br | C₂H₅ | SC₂H₅ | O | $n_D^{22}$ 1.5780 |
| 27 | C₆H₅— | H | H | C₂H₅ | SC₃H₇(n) | O | $n_D^{27}$ 1.5542 |
| 28 | C₆H₅— | H | H | C₂H₅ | SC₃H₇(n) | S | $n_D^{28}$ 1.5830 |
| 29 | C₆H₅— | H | Br | C₂H₅ | SC₃H₇(n) | O | $n_D^{27}$ 1.5682 |
| 30 | C₆H₅— | H | Cl | C₂H₅ | SC₃H₇(n) | O | $n_D^{20}$ 1.5616 |
| 31 | C₆H₅— | H | Cl | C₂H₅ | SC₃H₇(n) | S | $n_D^{30}$ 1.5834 |
| 32 | C₆H₅— | CH₃ | H | C₂H₅ | SC₃H₇(n) | O | $n_D^{30}$ 1.5475 |
| 33 | C₆H₅— | CH₃ | H | C₂H₅ | SC₃H₇(n) | S | $n_D^{28}$ 1.5748 |
| 34 | C₆H₅— | H | CH₃ | C₂H₅ | SC₃H₇(n) | O | $n_D^{24}$ 1.5538 |
| 35 | C₆H₅— | H | NO₂ | C₂H₅ | SC₃H₇(n) | O | mp 80–81° C. |
| 36 | Br—C₆H₄— | H | H | C₂H₅ | SC₃H₇(n) | O | $n_D^{25}$ 1.5635 |
| 37 | Cl—C₆H₄— | H | H | C₂H₅ | SC₃H₇(n) | O | $n_D^{27}$ 1.5599 |
| 38 | Cl—C₆H₄— | H | H | C₂H₅ | SC₃H₇(n) | S | $n_D^{28}$ 1.5922 |
| 39 | Cl—C₆H₄— | H | Cl | C₂H₅ | SC₃H₇(n) | O | $n_D^{25}$ 1.5654 |
| 40 | Cl—C₆H₄— | H | Cl | C₂H₅ | SC₃H₇(n) | S | $n_D^{25}$ 1.5777 |
| 41 | CH₃—C₆H₄— | H | H | C₂H₅ | SC₃H₇(n) | O | $n_D^{30}$ 1.5525 |
| 42 | CH₃—C₆H₄— | H | Cl | C₂H₅ | SC₃H₇(n) | O | $n_D^{20}$ 1.5581 |

EXAMPLE 3

| Emulsifiable concentrate | |
|---|---|
| Compound No. 30 | 20 wt. % |
| Xylene | 75 wt. % |
| Polyoxyethylene glycol ether (Nonipol 85 ®) | 5 wt. % |

The above components were admixed to prepare an emulsifiable concentrate.

EXAMPLE 4

| Wettable powder | |
|---|---|
| Compound No. 29 | 30 wt. % |
| Sodium ligninsulfonate | 5 wt. % |
| Polyoxyethylene glycol ether (Nonipol 85 ®) | 5 wt. % |
| Clay | 60 wt. % |

The above components were admixed to prepare a wettable powder.

EXAMPLE 5

| Dust | |
|---|---|
| Compound No. 38 | 3 wt. % |
| Clay | 96.6 wt. % |
| Silicone | 0.3 wt. % |
| Polyethylene glycol ether (Nonipol 85 ®) | 0.1 wt. % |

The above components were admixed to prepare a dust.

EXAMPLE 6

| Granule | |
|---|---|
| Compound No. 13 | 10 wt. % |
| Sodium ligninsulfonate | 5 wt. % |
| Bentonite | 85 wt. % |

The above components were kneaded with water to prepare granules.

EXAMPLE 7

Effect against *Laodelphax striatellus*

(a) Each test compound was formulated as in Example 3 and the emulsifiable concentrate thus obtained was diluted with water to prepare an emulsion of 40 ppm concentration. A test tube (1.7 cm in dia., 4 cm deep) was filled with 2.5 ml of the above emulsion and the roots of three paddy-rice seedlings 7 days after emergence) were immersed for 2 hours. The seedlings were transferred to a test tube containing 1 ml of water and ten 3-instar larvae of *Laodelphax striatellus* were released in the tube. The test tube was allowed to stand in a chamber (28° C.) and dead insects were counted. The test was performed in duplicate. The results, in terms of % mortality, are shown in Table 2.

TABLE 2

| Compound No. | % Mortality | Compound No. | % Mortality |
|---|---|---|---|
| 3 | 90 | 23 | 70 |
| 8 | 60 | 25 | 70 |
| 17 | 75 | 29 | 95 |
| 18 | 95 | 30 | 100 |
| 19 | 100 | 34 | 90 |
| 20 | 89 | 37 | 90 |
| 22 | 95 | Untreated Control | 0 |

The compound Nos. in Table 2 correspond to those used in Table 1.

TEST EXAMPLE 2

Effect against *Spodoptera litura*

(a) A 500 ppm aqueous dilution of each test compound (the emulsifiable concentrate of Example 3) (with Dyne ®, spreading agent, as diluted 3000-fold) was prepared and 20 ml of this dilution was sprayed over the soybean seedlings (10 days after emergence) water-cultured in a polyethylene cup using a spray gun (nozzle pressure 1 kg/cm$^2$) in a spray chamber.

Two hours after spraying, two leaves were shorn off and each was placed in a paper cup (6 cm in dia., 4 cm deep). Ten 2-instar larvae of *Spodoptera litura* were released in the cup, which was then placed in a room (25° C.). After 48 hours dead insects were counted. The test was performed in duplicate. The results, in terms of % mortality, are shown in Table 3 (I).

(b) One-hundred (100) mg. of the granules according to Example 8 were mixed into the soil adjacent to the root of a soybean plant in a pot (9 cm in dia.), which was then placed in a glass room (28° C.) Five days after treatment, two leaves of the soybean plant were shorn off and each was put in a paper cup. Ten 2-instar larvae of *Spodoptera litura* were released in the cup. The cup was allowed to stand in a room (25° C.) for 48 hours, at the end of which time dead insects were counted. The test was performed in duplicate. The test results, in terms of % mortality, are shown in Table 3 (II).

TEST EXAMPLE 3

Effect against *Unaspis yanonensis*

Each test compound was formulated as in Example 4 to prepare a wettable powder, which was then diluted with water (with Dyne ®, spreading agent, diluted 3000-fold) to obtain an aqueous suspension of 500 ppm concentration. Twenty (20) ml of this aqueous suspension was sprayed over 2-instar larvae (10 to 50 larvae) of *Unapsis yanonensis* on a trifoliate orange seedling (2 months after emergence) in a pot (9 cm in dia.). The pot was then placed in a greenhouse (25°-30° C.), and 20 days after spraying, adult insects were counted. The test was performed in duplicate. The results, in terms of % mortality, are shown in Table 4. The % mortality was computed by means of the following equation.

$$\% \text{ Mortality} = 100 - \frac{\text{No. of adults}}{\text{No. of 2-instar larvae}} \times 100$$

TABLE 3

| Compound No. | % Mortality I | % Mortality II | Compound No. | % Mortality I | % Mortality II |
|---|---|---|---|---|---|
| 1 | 100 | 100 | 21 | 100 | 70 |
| 2 | 100 | 100 | 22 | 100 | 0 |
| 3 | 100 | 30 | 23 | 100 | 0 |
| 4 | 100 | 100 | 24 | 100 | 30 |

TABLE 3-continued

| Compound No. | % Mortality I | % Mortality II | Compound No. | % Mortality I | % Mortality II |
|---|---|---|---|---|---|
| 5 | 100 | 100 | 25 | 100 | 5 |
| 6 | 100 | 20 | 26 | 100 | 0 |
| 7 | 100 | 100 | 27 | 100 | 0 |
| 8 | 100 | 100 | 28 | 100 | 0 |
| 9 | 100 | 45 | 29 | 100 | 0 |
| 10 | 100 | 100 | 30 | 100 | 0 |
| 11 | 100 | 100 | 31 | 100 | 0 |
| 12 | 100 | 100 | 32 | 100 | 0 |
| 13 | 100 | 100 | 33 | 100 | 0 |
| 14 | 100 | 0 | 34 | 100 | 0 |
| 16 | 100 | 20 | 35 | 100 | 0 |
| 17 | 100 | 5 | 37 | 100 | 0 |
| 18 | 100 | 100 | 38 | 100 | 0 |
| 19 | 100 | 0 | 41 | 100 | 0 |
| 20 | 100 | 0 | Untreated Control | 0 | 0 |

The compound Nos. in Table 3 correspond to those used in Table 1.

TABLE 4

| Compound No. | % Mortality | Compound No. | % Mortality |
|---|---|---|---|
| 2 | 79 | 23 | 100 |
| 5 | 100 | 24 | 91 |
| 6 | 100 | 25 | 70 |
| 7 | 93 | 27 | 84 |
| 10 | 94 | 29 | 100 |
| 15 | 92 | 30 | 83 |
| 17 | 93 | 34 | 90 |
| 20 | 82 | 37 | 80.3 |
| 21 | 89 | Untreated Control | 0 |

The compound Nos. in Table 4 correspond to those used in Table 1.

TEST EXAMPLE 4

Effect against Tetranychus urticae

Each test compound was formulated as in Example 3 to prepare an emulsifiable concentrate, which was then diluted with water (with Dyne®, spreading agent, diluted 3000-fold) to prepare an aqueous solution of 500 ppm concentration. A kidney-bean seedling, water-cultured in a polyethylene cup, was artificially infested with 10 female adults of Tetranychus urticae and the cup was allowed to stand in a glass room (28° C.) for 24 hours. Then, 20 ml of the above aqueous solution was sprayed over the kidneybean plant. After spraying, the cup was placed back in the glass room and the larvae and adults living on the leaves were counted 2 days and 7 days after spraying. The test was performed in duplicate. The percent decreases were computed by means of the following equation and the results were evaluated as follows. (See Table 5)

$$\text{Percent decrease} = \frac{\text{No. of test mites} - \text{No. of live larvae and adults at examination}}{\text{No. of test mites}} \times 100$$

| Rating of effects | Percent decrease |
|---|---|
| 0 | $\leq 20$ |
| 1 | 21–50 |
| 2 | 51–89 |
| 3 | $\geq 90$ |

TABLE 5

| Compound No. | Rating of Effects Day-2 | Rating of Effects Day-7 | Compound No. | Rating of Effects Day-2 | Rating of Effects Day-7 |
|---|---|---|---|---|---|
| 1 | 3 | 3 | 22 | 3 | 0 |
| 2 | 3 | 3 | 23 | 3 | 3 |
| 3 | 3 | 0 | 24 | 3 | 3 |
| 5 | 3 | 3 | 25 | 3 | 0 |
| 6 | 3 | 1 | 27 | 3 | 3 |
| 7 | 3 | 3 | 28 | 3 | 0 |
| 8 | 3 | 3 | 29 | 3 | 3 |
| 9 | 3 | 0 | 30 | 3 | 3 |
| 11 | 3 | 3 | 31 | 3 | 1 |
| 12 | 3 | 3 | 32 | 3 | 3 |
| 13 | 3 | 3 | 33 | 3 | 0 |
| 15 | 3 | 3 | 34 | 3 | 3 |
| 16 | 3 | 3 | 35 | 3 | 0 |
| 17 | 3 | 3 | 37 | 3 | 3 |
| 18 | 3 | 3 | 38 | 3 | 3 |
| 19 | 3 | 0 | 41 | 3 | 3 |
| 20 | 3 | 3 | | | |
| 21 | 3 | 3 | Untreated Control | 0 | 0 |

The compound Nos. in Table 5 correspond to those used in Table 1.

What is claimed is:

1. A compound of the formula:

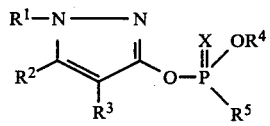

wherein $R^1$ is a straight-chain or branched alkyl of 1 to 4 carbon atoms, phenyl, or phenyl which is substituted by a halogen or a straight-chain or branched alkyl of 1 to 4 carbon atoms; $R^2$ is hydrogen; $R^3$ is hydrogen, a halogen, or a straight chain or branched alkyl of 1 to 4 carbon atoms; $R^4$ is ethyl; $R^5$ is n-propylthio; and X is oxygen.

2. A compound as claimed in claim 1, wherein $R^1$ is methyl, ethyl, n-propyl, isopropyl, n-butyl, sec-butyl, isobutyl, phenyl, 4-chlorophenyl or 4-methylphenyl; and $R^3$ is methyl, chlorine or bromine.

3. A compound as claimed in claim 1, namely O-ethyl-S-n-propyl-O-(1-phenyl-4-chloropyrazol-3-yl)phosphorothiolate.

4. A compound as claimed in claim 1, namely O-ethyl-S-n-propyl-O-(1-phenyl-4-bromopyrazol-3-yl)phosphorothiolate.

5. A compound as claimed in claim 1, namely O-ethyl-S-n-propyl-O-(1-isopropyl-4-methylpyrazol-3-yl)phosphorothiolate.

6. A compound as claimed in claim 1, namely O-ethyl-S-n-propyl-O-(1-sec-butylpyrazol-3-yl)phosphorothiolate.

7. A compound as claimed in claim 1, namely O-ethyl-S-n-propyl-O-(1-phenylpyrazol-3-yl)phosphorothiolate.

8. A compound as claimed in claim 1, namely O-ethyl-S-n-propyl-O-[1-(4-bromophenyl)pyrazol-3-yl]phosphorothiolate.

9. A compound as claimed in claim 1, namely O-ethyl-S-n-propyl-O-[1-(4-chlorophenyl)pyrazol-3-yl]phosphorothiolate.

10. A compound as claimed in claim 1, namely O-ethyl-S-n-propyl-O-[1-(4-chlorophenyl)-4-chloropyrazol-3-yl]phosphorothiolate.

11. A compound as claimed in claim 1, namely O-ethyl-S-n-propyl-O-[1-(4-methylphenyl)pyrazol-3-yl]phosphorothiolate.

12. A compound as claimed in claim 1, namely O-ethyl-S-n-propyl-O-[1-(4-methylphenyl)-4-chloropyrazol-3-yl]phosphorothiolate.

13. An insecticidal-acaricidal composition which comprises as an active component an insecticidally or acaricidally effective amount of a compound of the formula

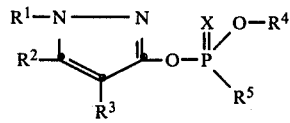

wherein $R^1$ is a straight-chain or branched alkyl of 1 to 4 carbon atoms, phenyl, or phenyl which is substituted by a halogen or a straight-chain or branched alkyl of 1 to 4 carbon atoms; $R^2$ is hydrogen; $R^3$ is hydrogen, a halogen, or a straight chain or branched alkyl of 1 to 4 carbon atoms; $R^4$ is ethyl; $R^5$ is n-propylthio; and X is oxygen, and a carrier therefor.

14. An insecticidal-acaricidal composition as claimed in claim 13, wherein $R^1$ is methyl, ethyl, n-propyl, isopropyl, n-butyl, sec-butyl, isobutyl, phenyl, 4-chlorophenyl or 4-methylphenyl; and $R^3$ is methyl, chlorine or bromine.

* * * * *